United States Patent
Andreoni et al.

(10) Patent No.: US 10,646,281 B2
(45) Date of Patent: May 12, 2020

(54) DEVICE AND METHOD FOR DETERMINING AN AXIS OF A RIGID BODY

(71) Applicant: ORTHOKEY ITALIA S.r.l., Carrara (Massa Carrara) (IT)

(72) Inventors: Gildo Andreoni, Fanano (IT); Simone Bignozzi, Bologna (IT)

(73) Assignee: ORTHOKEY ITALIA S.R.L. (IT)

( * ) Notice: Subject to any disclaimer, the term of this patent is extended or adjusted under 35 U.S.C. 154(b) by 109 days.

(21) Appl. No.: 15/764,483

(22) PCT Filed: Sep. 29, 2016

(86) PCT No.: PCT/IB2016/055833
§ 371 (c)(1),
(2) Date: Mar. 29, 2018

(87) PCT Pub. No.: WO2017/056034
PCT Pub. Date: Apr. 6, 2017

(65) Prior Publication Data
US 2018/0235712 A1    Aug. 23, 2018

(30) Foreign Application Priority Data
Sep. 30, 2015   (IT) .................. 102015000056601

(51) Int. Cl.
*A61B 34/20* (2016.01)
*A61B 17/15* (2006.01)

(52) U.S. Cl.
CPC ............ *A61B 34/20* (2016.02); *A61B 17/157* (2013.01); *A61B 2034/2048* (2016.02)

(58) Field of Classification Search
CPC ........ A61B 34/20; A61B 17/15; A61B 17/157
See application file for complete search history.

(56) References Cited

U.S. PATENT DOCUMENTS

| | | | |
|---|---|---|---|
| 10,258,256 B2* | 4/2019 | Mahfouz | ................ A61B 34/20 |
| 2011/0208093 A1* | 8/2011 | Gross | ................... A61B 5/4528 |
| | | | 600/587 |

OTHER PUBLICATIONS

PCT/IB2016/055833, Jan. 24, 2017, International Search Report and Written Opinion.

* cited by examiner

*Primary Examiner* — Christopher J Beccia
(74) *Attorney, Agent, or Firm* — Workman Nydegger

(57) ABSTRACT

It is disclosed a device for determining an axis joining origins of two reference systems of a rigid body. The device comprises first and a second inertial sensors constrained to the rigid body and for defining the first and second reference systems. The device comprises a processing unit comprising an acquiring module of first data of angular velocities and second data of linear accelerations of the rigid body, a first module for calculating third data of angular accelerations of the rigid body as a function of the first acquired data, a second module for calculating a relative orientation between the first and the second reference system as a function of the first data, a third module for calculating a vector joining origins of the first and second reference system, wherein the primary direction of the primary vector is representative of the axis joining the origins of the two reference systems.

13 Claims, 4 Drawing Sheets

DEVICE AND METHOD FOR DETERMINING AN AXIS OF A RIGID BODY

BACKGROUND

Technical Field

The present disclosure relates to a device for determining an axis joining origins of two reference systems.

In particular, the disclosure concerns a device able to determine an axis passing through two points of a rigid body, for example a bone.

Description of the Related Art

For a correct application of orthopaedic prostheses to an articulation it is of fundamental importance to precisely know the axis of the articular bones.

For the application of a knee prosthesis it is of fundamental importance to determine, with precision, the position and inclination of the axis of the tibia with respect to the tibial plateau.

The prosthesis comprises, in fact, a tibial component which is associated to the proximal end of the tibia, after having carried out a plane resection of a portion of the proximal end.

In order for the prosthesis to work correctly, it is essential for the plane resection to have a determined inclination with respect to the axis of the tibia.

The resection of the tibia is implemented with the aid of a cutting guide which is fixed to the bone in proximity of the tibial plateau.

The cutting guide is orientable in the space so as to allow orientating the resection plane in a desired way.

In order to regulate the orientation of the cutting guide, various mechanical devices are at present available that must be fixed to the tibia at least at two zones, typically the malleoli and the proximal end.

The fixing to the malleoli and the proximal end allows approximately to identify the longitudinal axis of the tibia, and thus to regulate the orientation of the cutting guide with respect to the identified axis.

The devices at present available have, however, numerous drawbacks.

First of all, the determination of the tibia axis is not particularly precise.

A further drawback is represented by the fact that the known-type devices allow orientating the resection plane with precision on the frontal plane (varus\valgus), but in a less precise way the inclination on the sagittal plane (slope).

Devices exist on the market that are not purely mechanical, but are based on inertial sensors that require particular operations to function with efficiency.

For example, some require registration of the significant anatomical landmarks, while others require a movement of the leg into determined positions.

BRIEF SUMMARY

The aim of the present disclosure is to provide a device and a method for determining an axis joining the origins of two reference systems, for example referred to a bone or a bone segment, which allows to overcome the drawbacks of the devices actually available.

The aim is achieved by a device for determining an axis joining origins of two reference systems of a rigid body.

The device comprises at least a first and a second inertial sensor, provided with a triaxial accelerometer and a triaxial gyroscope, arranged to be constrained to said rigid body and for respectively defining the first and the second reference system.

The device further comprises a processing unit, connected to the inertial sensors, comprising:

an acquiring module configured to acquire first data representing angular velocities and second data representing linear accelerations of the rigid body detected by the first and second inertial sensor during a movement of the rigid body itself;

a first calculating module configured to calculate third data representing angular accelerations of the rigid body as a function of the first data acquired;

a second calculating module configured to calculate a relative orientation between the first and the second reference system as a function of the first data;

a third calculating module configured to calculate a vector which joins origins of the first and of the second reference system as a function of said first, second and third data and as a function of the relative orientation calculated between the first and the second reference system, wherein the primary direction of the primary vector is representative of the axis joining the origins of the two reference systems.

The above indicated aim is also achieved by a method for determining an axis joining origins of two reference systems of a rigid body.

The determination method comprises the steps of:

a) providing, on the rigid body, at least a first and a second inertial sensor, provided with a triaxial accelerometer and a triaxial gyroscope;

b) constraining the first and second inertial sensor to the rigid body to respectively define the first and second reference system;

c) moving the rigid body so as to determine an angular displacement of the rigid body;

d) acquiring, by means of the first and second inertial sensor, first data representing angular velocities and second data representing linear accelerations of the rigid body during the movement of the rigid body;

e) calculating third data representing angular accelerations of the rigid body as a function of the first data acquired;

f) calculating a relative orientation between the first and the second reference system as a function of the first data;

g) determining a primary vector which joins the origins of the first and of the second reference system as a function of the first, second and third data and as a function of the relative orientation calculated between the first and second reference system, wherein the primary direction of the primary vector is representative of the axis joining the origins of the two reference systems.

One embodiment of the present disclosure is a computer program comprising software code portions adapted to perform the steps d)-g) of the determination method.

Advantageous aspects are described in the dependent claims.

An advantage of the present disclosure is that it allows determining the axis of a rigid body, and in particular of a bone, with a significantly greater precision with respect to the devices actually available.

A further advantage of the present disclosure is to be much faster for applying and using that the devices actually available, allowing drastic reduction of operating times.

A further advantage of the present disclosure is that it allows applying a very precise correction to the varus/valgus angles and/or extension/flexion of the articulation.

A further advantage is that the device implements an instrument set that is significantly compact and implements a registration procedure that is faster and more immediate, less subject to human error.

Further characteristics and advantages of the present disclosure will become more apparent in the following detailed description of an embodiment of the present disclosure, illustrated by way of non-limiting example in the attached figures, wherein:

DETAILED DESCRIPTION

Note that the disclosure is not limited to the determining of an axis joining two points of a bone, but it can be applied more generally for determining an axis joining the origins of two reference systems of any rigid body T of which the relative positions and orientation are not priorly known, as will be explained in greater detail at the end of the description.

Figure 1:
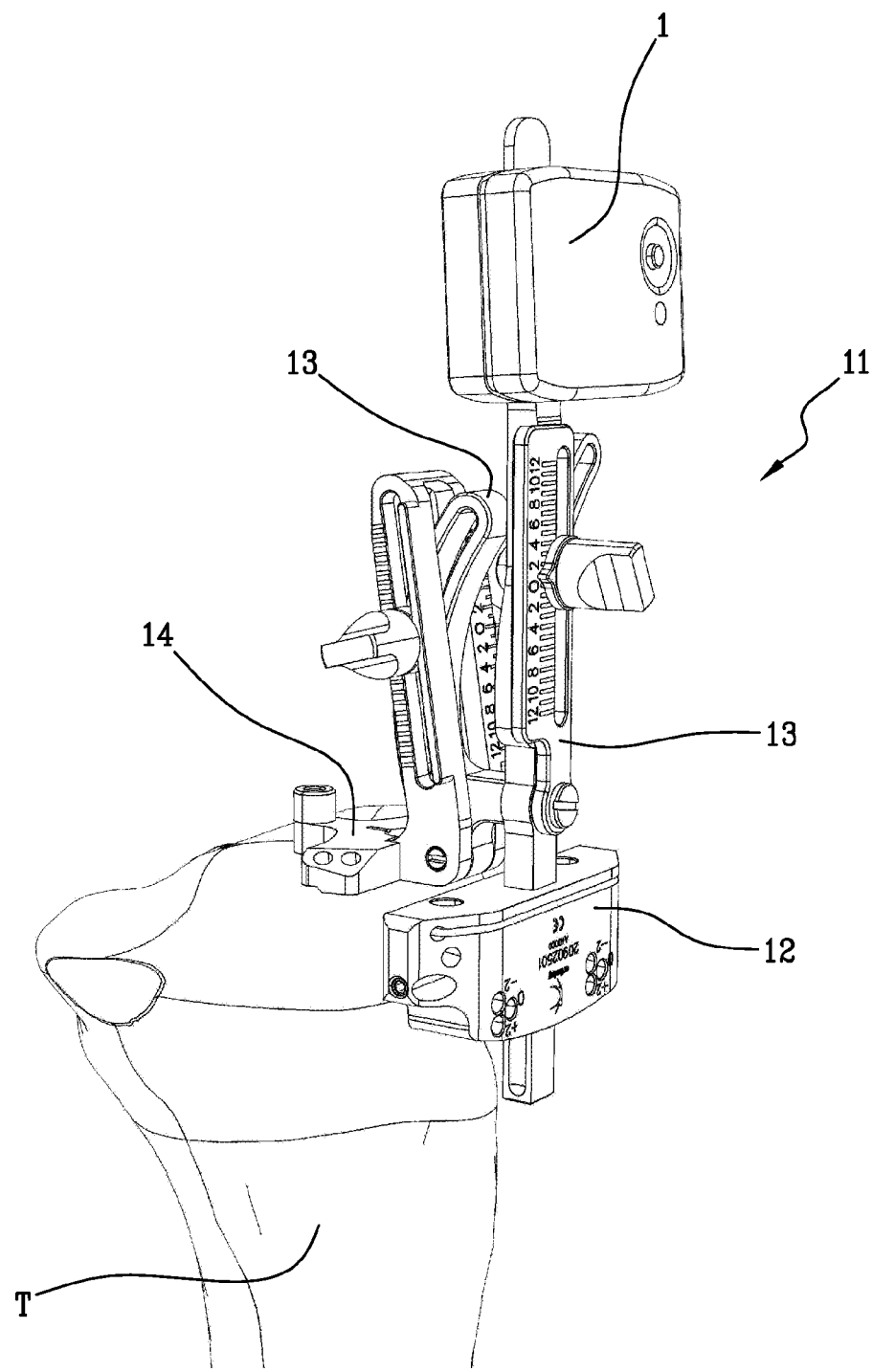
FIG. 1 schematically shows a fixing component of the device according to the present disclosure, applied to a tibia.
Figure 2:
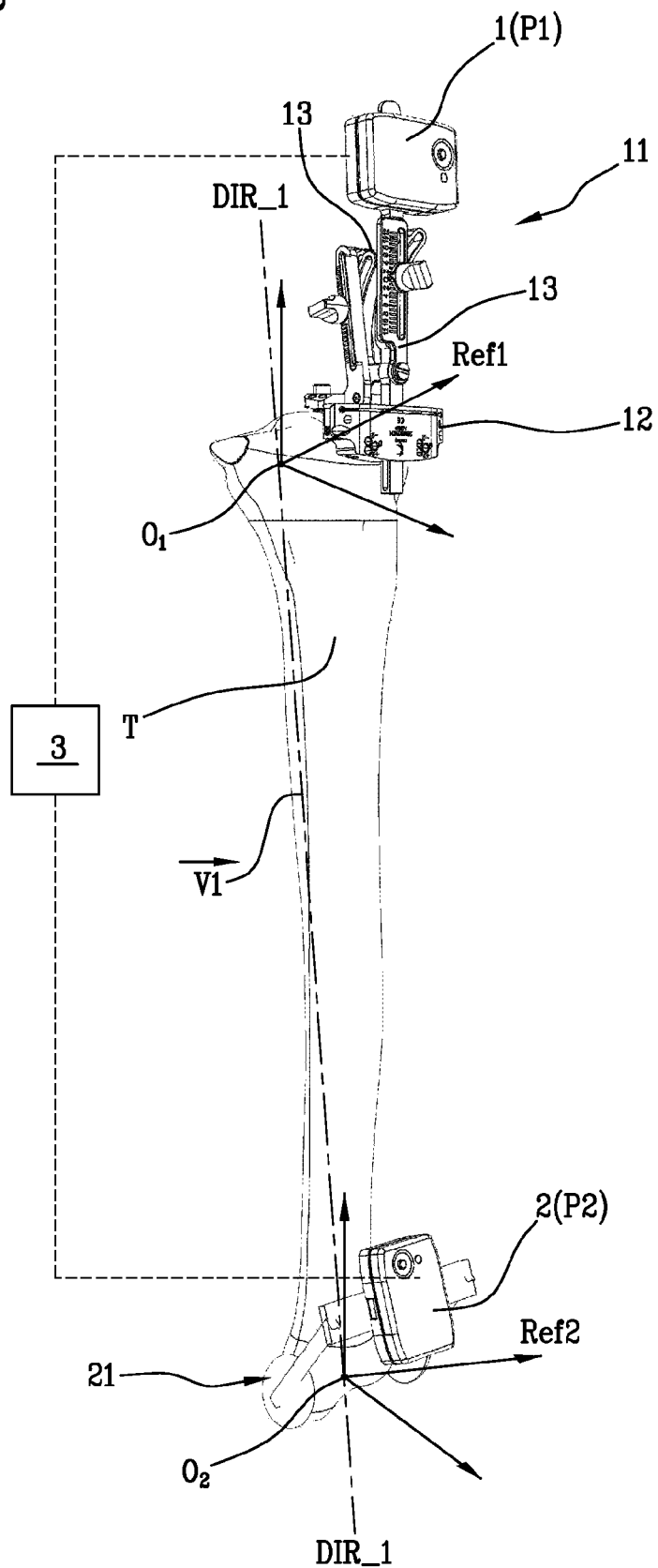
FIG. 2 shows the device according to the present disclosure applied to a tibia.

For the purposes of the explanation of the disclosure, for the sake of simplicity the rigid body T is considered to be a tibia, as illustrated in FIGS. 1 and 2.

A first fixing component 11 is fixed invasively to the proximal part of the tibia T and a second fixing component 21 is fixed in a non-invasive way to the distal part of the tibia T.

The first fixing component 11 is composed of three parts:
- an orthopaedic fixing system 14 fixed to the tibial plateau with one or more surgical pins;
- a cutting guide 12 comprising a cutting tool (for example a surgical saw) to perform a bone resection of the tibial plateau;
- a regulating device 13 which connects the cutting guide 12 to the fixing system 14, for allowing to modify the orientation in the space of the cutting guide 12 with respect to the orthopaedic fixing system 14.

A first inertial sensor 1 is solidly constrained, in terms of orientation, to the cutting guide 12, which can instead slide along a stem.

The second fixing component 21 is for example an anklet fixed to the malleoli in a non-invasive way and is equipped with a second inertial sensor 2.

With particular reference to FIG. 2, the device according to the present disclosure comprises at least the first and second inertial sensor 1, 2, each one equipped with a triaxial accelerometer and a triaxial gyroscope, arranged to be constrained to a rigid body T, in particular a bone, and for respectively defining a first Ref1 and a second Ref2 reference system, in particular in three-dimensional coordinates useful for determining a reference system of the bone itself.

Various models of inertial sensor are currently available, provided for defining a three-dimensional coordinate system, all within the scope of the technical expert of the sector, and will thus not be described in detail.

It is noted that the first reference system Ref1 is not centred on the first inertial sensor 1, but the relative position is known (and constant) as well as the relative orientation with respect to the reference system centred on the first sensor 1, as will be explained in greater detail in the following; likewise, the second reference system Ref2 is not centred on the second inertial sensor 2, but the relative position is known (and constant) as well as the relative orientation with respect to the reference system centred on the second sensor 2, as will be explained more in detail in the following.

More in detail, the matrix of dimensions 4x4 will be referred to as the transformation matrix (or transform) between two reference systems, which allows expressing:
- the relative orientation between the axes of two reference systems;
- the coordinates of the vector joining the origins of the two reference systems.

In the particular case, two reference systems Ref1, Ref2 are defined in the following way:
- the first reference system Ref1 originates in the centre of the tibial plateau, so that the transform between the first reference system Ref1 and the reference system centred on the first inertial sensor 1 is constant and known;
- the first reference system Ref2 originates in the intermediate point between the two malleoli of the ankle, so that the transform between the second reference system Ref2 and the reference system centred on the second inertial sensor 2 is constant and known.

Consequently, the first reference system Ref1 is solidly connected to the reference system centred on the first inertial sensor 1, as the relative position and orientation are known and constant; likewise, the second reference system Ref2 is solidly connected to the reference system centred on the second inertial sensor 2, as the relative position and orientation are known and constant.

Still with reference to FIG. 2, the device of the disclosure comprises a processing unit 3.

In general, it should be noted that in the present context and in the subsequent claims, the processing unit 3 is presented as being divided into distinct functional modules (storage modules or operative modules) for the sole purpose of describing its functionalities clearly and completely.

In actual fact, this processing unit 3 can comprise a single electronic device, appropriately programmed to perform the functionalities described, and the different modules can correspond to hardware entities and/or routine software that are part of the programmed device.

Alternatively, or in addition, these functions can be performed by a plurality of electronic devices over which the above-mentioned functional modules can be distributed.

The processing unit 3 can also make use of one or more processors for executing the instructions contained in the storage modules.

The aforementioned functional modules can also be distributed on different local or remote calculators, depending on the architecture of the network in which they reside.

The processing unit 3 is connected to the inertial sensors 1, 2, for receiving in input the data and determining corresponding processing.

The connection between the processing unit 3 and the inertial sensors 1, 2 can be of any type, either cable or wireless.

In particular, the processing unit 3 is configured to acquire the data of angular velocity and linear acceleration detected by the inertial sensors 1, 2 during an arbitrary movement of the rigid body T, and it is configured to calculate the angular acceleration, for example by means of the derivative of the angular velocity.

The term "arbitrary movement" of the rigid body T means a rotation and/or translation movement that is not constrained along a determined direction or plane, and wherein said movement is sufficient to determine remarkable measurements from of the inertial sensors 1, 2.

Figure 3A:
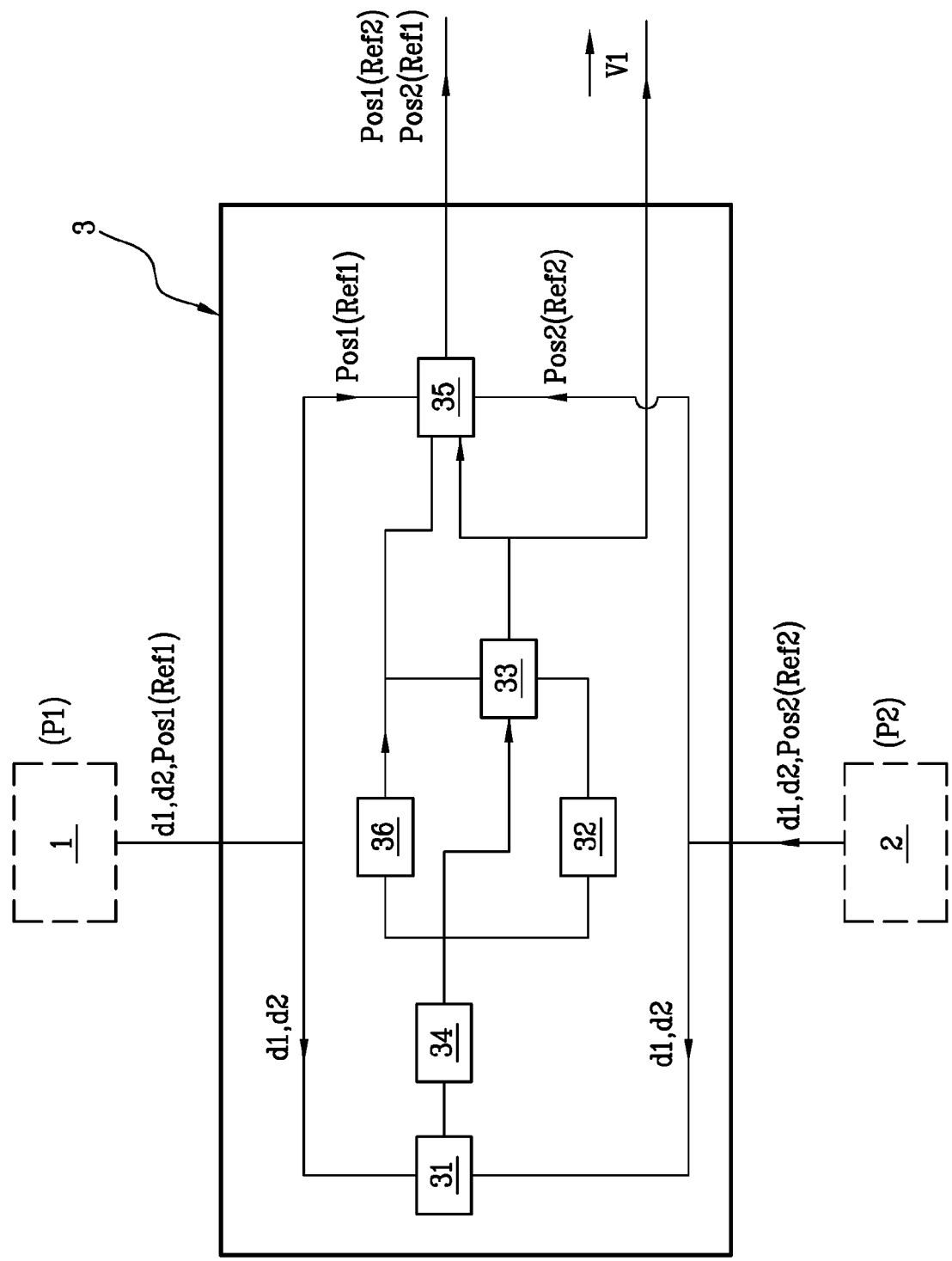
FIG. 3A shows a block diagram of the processing unit of the device according to a first embodiment of the disclosure.

With specific reference to FIG. 3A, the processing unit 3 comprises an acquiring module 31 (i.e. a collector) configured to acquire first data d1 representing angular velocities and second data d2 representing linear accelerations of the rigid body T detected by the inertial sensors 1, 2 during an arbitrary movement of the rigid body T itself.

Note that the first data d1 represent values of linear acceleration acquired by means of accelerometers present in the inertial sensors 1, 2, in general, said acquired values also comprise a component of gravitational acceleration.

In one embodiment, it is possible to remove the component of gravitational acceleration by means of an estimation of the orientation of the inertial sensors 1, 2 with respect to a terrestrial inertial reference system, thus obtaining only the linear acceleration component caused by the movement of the rigid body T.

Therefore for the purposes of explanation of the disclosure, the term "first data d1 representing linear accelerations" means the value of linear acceleration detected by the accelerometers of the two inertial sensors 1, 2, without the component of the gravitational acceleration.

In one embodiment, the processing unit 3 further comprises a compensating module 34 (i.e. a compensator) configured to compensate a phase shift between the signals detected by the inertial sensors 1, 2: this allows improving the reliability of the measurements, as it allows temporally synchronising the data acquired by the two inertial sensors 1, 2, each comprising the first d1 and second d2 data.

Said compensation, in fact, is useful in case wherein no synchronisation at hardware level is provided between the first inertial sensor 1 and the second inertial sensor 2, or when the device used for performing the acquisition (for example, a commercial processor connected via Bluetooth) is not able to ensure exchange of real-time data.

The acquisition frequency of the first inertial sensor 1 and of the second inertial sensor 2 is fixed (i.e. it is constant) and is timed also between different devices.

In case of acquisition between two or more inertial sensors having a same acquisition frequency, it is thus necessary to estimate the phase shift existing between the two or more acquisitions.

For this purpose it is useful to observe that the two or more installed inertial sensors are solidly constrained to the rigid body T.

Therefore the values of the Euclidean norm of the vectors of the angular velocities in a determined instant must be equal in the two or more acquisitions coming from the two or more inertial sensors.

Considering in particular the case of the two inertial sensors 1, 2, it is possible to obtain two scalar vectors equal to the values of the Euclidean norm of the vectors of the angular velocities acquired in a determined time interval Δt; in this case the obtained signals will have the same shape, but will be probably phase-shifted from one another.

It is therefore possible to determine the phase shift present on the two signals acquired by the sensors 1, 2, minimising the difference between the values of the Euclidean norm of the vectors of the angular velocities, on varying the phase shift.

The calculated phase shift on the signal d1 will be applicable also to the signal d2, as they are quantities acquired at the same time.

The processing unit 3 further comprises a first calculating module 32 (i.e. a first calculator) configured to calculate third data d3 representing angular accelerations of the rigid body T as a function of the first data d1 acquired.

In particular, the third data d3 representing angular accelerations of the rigid body T are calculated by means of the derivative operation of the first data d1 representing the angular velocities of the rigid body T.

The processing unit 3 further comprises a second calculating module 36 (i.e. a second calculator) configured to calculate a relative orientation between the first reference system Ref1 and the second reference system Ref2 as a function of the data d1.

In particular, the relative orientation is expressed by means of a rotation matrix MR defined as a function of the first data d1.

In one embodiment, the relative constant orientation between the first Ref1 and the second Ref2 reference system is determined in the following way.

The first and second sensor 1, 2 (to which the first Ref1 and the second Ref2 reference system are associated) are solidly constrained to the rigid body T.

In this hypothesis the vectors of the angular velocities (possibly synchronised by means of the compensating module 34) acquired by the two sensors 1, 2 in a determined instant are theoretically equal in case wherein the two reference systems Ref1, Ref2 are orientated identically (i.e. if they have the respective reference Cartesian axes parallel).

In case wherein this condition is not fulfilled, the values of the Euclidean norm of the vectors of the two angular velocities acquired by the two inertial sensors 1, 2 are equal, but the orientation between the reference systems centred on the two inertial sensors 1, 2 is different and thus there will be a different vector decomposition of the two angular velocities acquired on the 3 reference Cartesian axes; it is possible to exploit this to determine the relative constant orientation between the two reference systems Ref1, Ref2, by analysing the direction of the vectors of the angular velocities acquired by the two sensors 1, 2 in a determined time interval.

The technical effect is a precise obtaining the relative orientation between the reference systems Ref1, Ref2 defined by the sensors 1, 2.

This further allows preventing use of magnetometers which are not allowed in operating rooms because of the excessive interference possible with surgical instruments, while unambiguously determining the 3 degrees of freedom which express the relative orientation between the sensors.

In particular, each of the inertial sensors 1, 2 comprises:
- a triaxial gyroscopic detection unit, for example with a 16-bit output, full-scale configurable at ±250/±500/±2000°/s,
- a triaxial accelerometer detection unit, for example with a 12 or 16 digital output programmable between ±2 g/±6 g, and
- a Bluetooth module that incorporates a firmware able to emulate a serial connection (not natively available in the Bluetooth 4.0 protocol), in particular for a communication via UART on mobile or PC devices.

Therefore the implemented sensors 1, 2 allows to perform a streaming of accelerometer and gyroscopic data at a automatically scalable frequency according to the quality of the Bluetooth connection, for example between the values of 60, 90 and 120 Hz.

The processing unit 3 further comprises a third calculating module 33 (i.e. a third calculator) configured to calculate a primary vector V1 which joins the origin $O_1$ of the first reference system Ref1 with the origin $O_2$ of the second reference system Ref2, as a function of the first data d1, of the second data d2, of the third data d3 and of the relative orientation between the first reference system Ref1 and the second reference system Ref2, wherein the relative orientation was calculated previously by the second calculating module 36.

In one embodiment, the primary direction DIR_1 of the primary vector V1 is representative of the axis joining the origins of the two reference systems Ref1, Ref2.

In other words, the processing unit 3 runs a calculating algorithm which performs the processing of data of the angular velocity, angular acceleration, linear acceleration detected by the inertial sensors 1, 2 during a movement of the rigid body and the processing of the relative orientation between the first reference system Ref1 and the second reference system Ref2, so as to identify the primary vector V1 which joins the origin $O_1$ of the first reference system with the origin $O_2$ of the second reference system.

The calculations include the analysis of these data considering the motion of the rigid body T as a rotation about a point of variable coordinates (centre of instantaneous rotation).

The processing unit 3 comprises a transforming module 35 (i.e. a converter) configured to:
  receive in input data representing the reference systems Ref1, Ref2, one or more points Pos1, Pos2 in the corresponding reference systems Ref1, Ref2, the relative orientations between the reference systems Ref1 and Ref2, the vector V1 calculated by the module 33 and
  transform a point Pos1, Pos2 from a first of the reference systems Ref1, Ref2 towards a second of the reference systems Ref1, Ref2.

In other words, the transforming module 35 calculates a transformation matrix between the first Ref1 and the second Ref2 reference system.

With the transformation matrix known, the coordinates of the second reference system can be expressed in coordinates relative to the first reference system by applying the transformation matrix to the coordinates of the second reference system.

Still in other words, given a point Pos1(Ref1) in the first reference system, the transforming module 35 calculates the point Pos1(Ref2) in the second reference system; likewise, given a point Pos2 (Ref2) in the second reference system, the transforming module 35 calculates the point Pos2(Ref1) in the first reference system.

The technical effect obtained is the quick and precise determining of the position and orientation of any straight line passing through a point Pos1 the coordinates of which are known in the first reference system and for a point Pos2 the coordinates of which are initially known in the second reference system.

The device of the present disclosure allows defining an axis passing through two points of a rigid body, for example a bone segment or a bone.

By placing the first inertial sensor 1 in a first position of the rigid body T and the second inertial sensor 2 in a second position of the rigid body T, it is sufficient to arbitrarily move the rigid body in the space in order to obtain the coordinates of any point located in the second reference system expressed in coordinates of the first reference system. This therefore allows defining, with respect to the first reference system, the position and inclination of any straight line passing through a point belonging to the first reference system and for a point belonging to the second reference system.

The disclosure also discloses a method for determining an axis of a rigid body.

The method of determining an axis joining the origins of two reference systems Ref1, Ref2 of a rigid body T according to the disclosure includes:
  providing, on the rigid body T, at least a first and a second inertial sensor 1, 2, provided with a triaxial accelerometer and a triaxial gyroscope;
  constraining the first and second inertial sensor 1, 2 to the rigid body T to respectively define said first Ref1 and second Ref2 reference system;
  arbitrarily moving the rigid body T so as to determine an angular displacement of the rigid body T;
  acquiring first data d1 representing angular velocities and second data d2 representing linear accelerations of the rigid body T detected by the inertial sensors 1,2 during the arbitrary movement of the rigid body T,
  calculating third data d3 representing angular accelerations of the rigid body T as a function of the first data d1 acquired;
  calculating a relative orientation between the first and the second reference systems Ref1 and Ref2 as a function of the first data d1;
  calculating a primary vector V1 which joins the origins O1, O2 of the first Ref1 and the second Ref2 system of coordinates as a function of the first, second and third data d1, d2, d3 and of the calculated orientation between reference system Ref1 and Ref2, wherein the primary direction DIR_1 of the primary vector V1 is representative of the axis joining the origins O1, O2 of the two reference systems Ref1, Ref2.

The processing unit 3 receives in input data representing said reference systems Ref1, Ref2, one or more points Pos1, Pos2 of the corresponding reference systems Ref1, Ref2, and transforms a point Pos1, Pos2 from a first of the reference systems Ref1, Ref2 towards a second of the reference systems Ref1, Ref2.

The method further includes compensating a possible delay, by means of the compensating module 34, between the flows of data detected by the inertial sensors 1, 2, determining a synchronisation in input to the third calculating module 33 of the first and second data d1, d2 previously acquired by the acquiring module 31.

The method further comprises the steps of:
  providing a first fixing component 11 structured for being fixed the rigid body, in particular, but not limitedly, to an end thereof;
  providing a cutting guide 12, structured to house a cutting tool and to maintain the cutting tool in a constant orientation;
  providing a regulating device 13 structured to connect the cutting guide 12 to the orthopaedic fixing system 14, wherein the first inertial sensor 1 is mounted in a first position P1 solidly constrained, in terms of orientation, to the cutting guide 12;
  providing a second fixing component 21 structured to be fixed to the rigid body T at a second inertial sensor 2 in a second position P2 different from the first position P1.

In one embodiment, it is provided a step of regulating the orientation in the space of the cutting guide 12 with respect to the orthopaedic fixing system 14, to the second fixing component 21 and as a function of the calculated vector V1, by means of the regulating device 13.

In a particularlembodiment, the rigid body T is a bone, in particular a tibia.

As an aid for defining the axis of a bone, for example the mechanical axis of the tibia, the device comprises the first fixing component 11, provided to be fixed to a bone or an anatomical part of a limb, for example the proximal end of the tibia.

The first inertial sensor 1 is associated to the first fixing component 11 and is mounted in a position P1 solidly constrained, in terms of orientation, to the cutting guide 12.

The first fixing component 11 can be fixed to the tibial plateau in a known way by one or more pins, by means of the orthopaedic fixing system 14.

The device further comprises the second fixing component 21 to which the second inertial sensor 2 is associated.

The second fixing component 21 is structured for being fixed to the rigid body T, in particular a bone or an anatomical part of a limb, in a second position P2 different from the first position P1, in particular to the distal end of the tibia, preferably in proximity of the malleoli.

In one embodiment, the second fixing component 21 comprises a pliers structured to be fixed to the malleoli.

In particular, the pliers is structured to vary the distance between the jaws thereof, without modifying, with respect to the second reference system Ref2, the position of a central point between the same jaws. This central point has known coordinates relative to second reference system, i.e. relative to the reference system defined by the second inertial sensor 2.

Alternatively, the second fixing component 21 might vary the position of the central point between the jaws in a predetermined way. In this case the calculation algorithm is structured to take into account of the displacement of the central point between the jaws.

The determination of the direction of the mechanical axis DIR_1 of the tibia can be obtained by knowing the coordinates with respect to the first reference system Ref1 of two significant points: the midpoint of the tibial plateau Pos1 and the midpoint of the malleolar axis Pos2.

The coordinates of the midpoint of the tibial plateau are known for construction of the device; the coordinates of the midpoint of the malleolar axis with respect to the first reference system can be calculated in the way described, by moving the tibia in tge space once the two inertial sensors 1, 2 are applied.

The fixing device of the disclosure comprises a cutting guide 12, arranged for maintaining a cutting tool in a constant orientation, and can be associated, or coupled, to the first fixing component 11.

In particular, the cutting guide 12 can be connected to the first fixing component 11 by means of a regulating device 13, known in the sector, structured to connect the cutting guide 12 to the first fixing component 11 and to allow a regulating of the orientation in space of the cutting guide 12 with respect to the orthopaedic fixing system 14.

In particular, the regulating of the orientation in the space of the cutting guide 12 is performed with respect to the orthopaedic fixing system 14, to the second fixing component 21 and as a function of the calculated vector V1, by means of the regulating device 13.

In one embodiment, the first inertial sensor 1 is solidly constrained, in terms of orientation, to the cutting guide 12.

In this way, with the position and inclination of the axis of the tibia known with respect to the first reference system, i.e. with respect to the first inertial sensor 1, it is possible to adjust the position of the cutting guide 12 for performing the resection of the proximal end of the tibia according to a desired inclination plane, with the aim of realising a seating for a prosthesis which has a predetermined inclination.

It is also possible to verify, with a second acquisition, whether the cutting guide 12 is correctly aligned after having adjusted the cutting guide 12 in space by acting on the graduated calipers.

In particular, by means of trigonometric functions, the processing unit 3 is able to calculate the orientation on the frontal plane and the sagittal plane of the bone. These angles can be communicated or shown to the surgeon who by using the regulating device 13 will adjust the orientation of the cutting guide 12 so as to realise the desired resection.

In one embodiment, the calculating algorithm is provided to compensate for a constant delay between the data flows detected by the inertial sensors 1, 2. This allows synchronising the acquisitions received from the two sensors and improves the reliability of the processing.

In particular, the processing unit 3 comprises a compensating module 34 configured to compensate a delay between the flows of data detected by the inertial sensors 1, 2 determining a synchronisation, in input to the first calculating module 32 and the second calculating module 36 of the first and second data d1, d2 (previously acquired by the acquiring module 31).

Figure 3B:
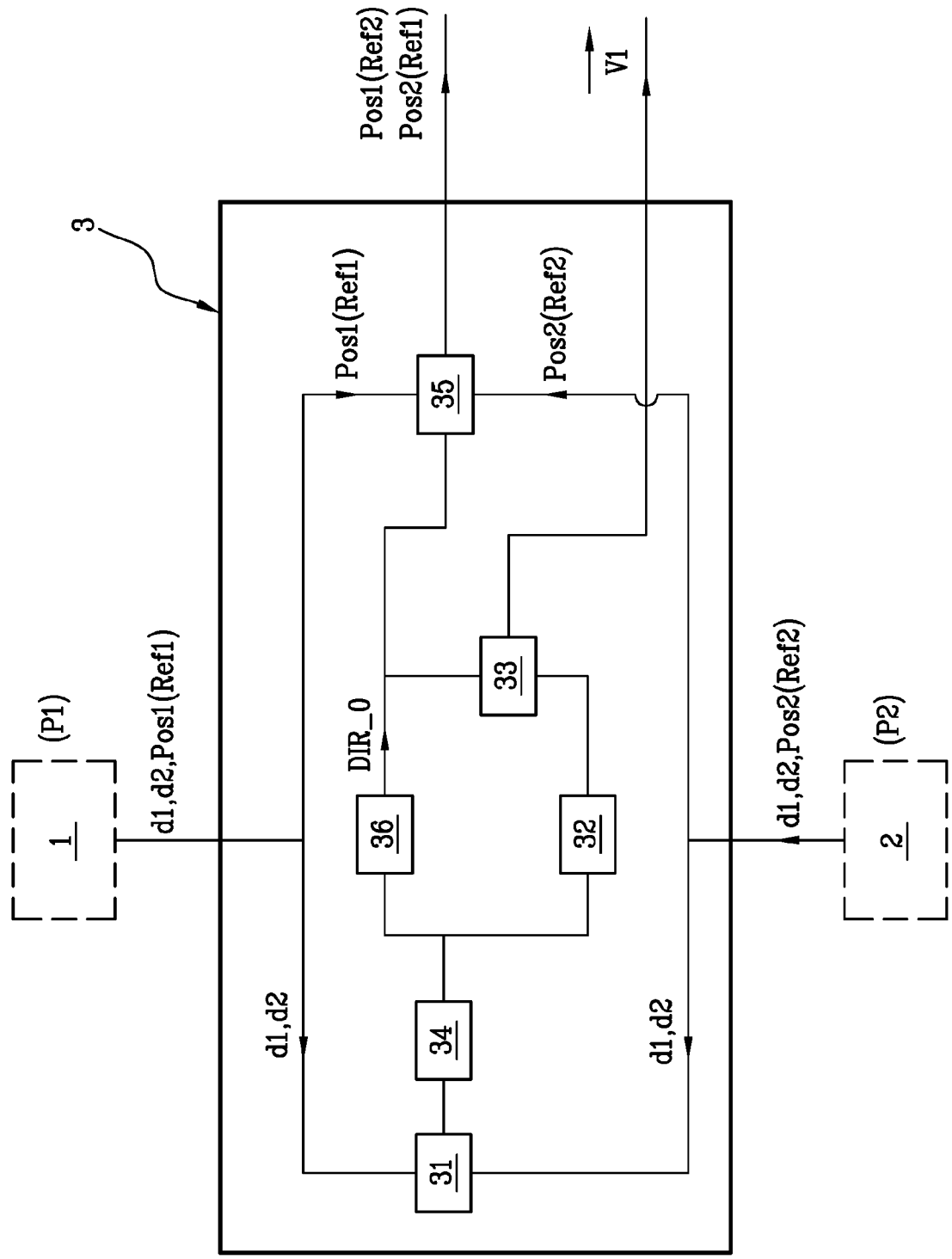
FIG. 3B shows a block diagram of the processing unit of the device according to a second embodiment of the disclosure.

With reference to FIG. 3B, it shows a block diagram of the processing unit 3 of the device according to a second embodiment of the disclosure.

FIG. 3B differs from FIG. 3A in that:
the first calculating module 32 is configured to calculate third data d3 representing angular accelerations of the rigid body T as a function of the first and second acquired data d1, d2 representing angular velocities and linear accelerations respectively of the rigid body T;
the second calculating module 36 is configured to calculate a relative orientation DIR_0 between the inertial sensors 1 and 2, as a function of the third data d3;
the third calculating module 33 is configured to calculate the primary vector V1 which joins the origins of the first Ref1 and of the second Ref2 reference system as a function of the first data d1, second data d2 and third data d3 and as a function of the relative orientation DIR_0 between the inertial sensors 1, 2, wherein the primary direction DIR_1 of the primary vector V1 is representative of the axis joining the origins of the two reference systems Ref1, Ref2.

In one embodiment, also in the second embodiment the first and second data acquired d1, d2 are synchronised by means of the compensating module 34.

In particular, in the second embodiment the relative orientation between the inertial sensors 1 and 2 is expressed by means of a rotation matrix MR defined as a function of the first data d1 and of the second data d2.

In particular, in the second embodiment the transforming module 35 is configured to receive in input data representing the reference systems Ref1, Ref2, one or more points Pos1, Pos2 in the corresponding reference systems Ref1, Ref2, the relative orientation DIR_0 between the inertial sensors 1 and 2, and it is configured to transform a point Pos1, Pos2 from a first of the reference systems Ref1 and Ref2 towards a second of the reference systems Ref1, Ref2.

The device according to the present disclosure provides important advantages.

First of all, the absence of any mechanical connection between the inertial sensors 1, 2 significantly facilitates the use of the device, by substantially simplifying the application: this allows to drastically reduce intervention times.

Further, the use of two inertial sensors and a specific algorithm to place in relation and process the angular velocity data, linear acceleration and angular acceleration makes the identification of the sought axis extremely precise; further, the device implements an instrument set that is significantly compact and performs a registration procedure that is faster and more immediate, less subject to human error.

The disclosure can also be used in applications different than surgery.

In fact, by means of the device and of the method of the disclosure, the following information can be obtained:
- a vector joining the origins of the reference systems associated to the inertial sensors;
- the relative orientation between the axes of two reference systems associated to the inertial sensors;
- a vector joining two or more points the coordinates of which are known in reference systems associated to different inertial sensors;
- the coordinates of one or more points in a first reference system, initially expressed in a second reference system.

Said information allows using the device and method of the disclosure in every field wherein it is necessary to determine the axis passing through two or more points of a rigid body, even very distant each another.

In this case two or more inertial sensors are applied, in proximity of the points of interest, providing the sensors so as to know the coordinates between the reference systems associated thereto and the points of interest.

By means of the analysis of the data acquired during an arbitrary movement of the rigid body, it is possible to determine the above indicated information.

The estimation of the relative orientation between the reference systems associated to the inertial sensors, together with the estimation of the coordinates between the origins of the reference systems, determine the relative homogeneous transform between the above-mentioned reference systems.

Said transform allows obtaining complete information on the orientation and the relative position between different reference systems associated to a rigid body.

An example of application is one relating to an indoor localisation device on a large-dimension structure in movement, assimilable to a rigid body (for example a ship).

In this case it is possible to determine the position and relative orientation between different reference systems associated to a plurality of inertial sensors by means of the device and the method of the disclosure.

These inertial sensors can for example be fixed internally to containers or other objects to be localised.

Alternatively, these objects might consist of passengers' smartphones, usually equipped with accelerometers and gyroscopes, using the data acquired at instants wherein there is no relative movement between the ship and the passenger.

The data acquired by the sensors during navigation can be used to localise the inertial sensors with respect to a known reference system solidly constrained to the rigid body.

This solution, though applicable in a special context (a ship in motion) might compensate for the impossibility of GPS-based positioning in indoor environments.

The invention claimed is:

1. A device for determining an axis joining origins of first and second reference systems of a rigid body whose relative positions and orientation are not priorly known, the device comprising:
- a first inertial sensor and a second inertial sensor, each provided with a triaxial accelerometer and a triaxial gyroscope, arranged to be constrained to said rigid body and for respectively defining the first and the second reference system;
- a processing unit, connected to the inertial sensors, comprising:
  - an acquiring module configured to acquire first data representing angular velocities and second data representing linear accelerations of the rigid body detected by the first and second inertial sensors during a movement of the rigid body itself;
  - a first calculating module configured to calculate third data representing angular accelerations of the rigid body as a function of the acquired first data;
  - a second calculating module configured to calculate a relative orientation between the first and the second reference system as a function of the first data; and
  - a third calculating module configured to calculate a vector which joins origins of the first and of the second reference system as a function of said first, second and third data and as a function of the relative orientation calculated between the first and the second reference system, wherein a primary direction of a primary vector is representative of the axis joining the origins of the first and second reference systems;
- a first fixing component fixed to a first end of the rigid body, wherein the first fixing component comprises:
  - a fixing system fixed to the first end of the rigid body with one or more pins;
  - a cutting guide comprising a cutting tool and maintaining the cutting tool in a constant orientation;
  - a regulating device structured to connect the cutting guide to the fixing system and to modify the orientation in the space of the cutting guide with respect to the fixing system;
  - wherein the first inertial sensor is mounted in a first position solidly constrained, in terms of orientation, to the cutting guide;
- a second fixing component structured to be fixed to a second end of the rigid body at the second inertial sensor positioned in a second position different from the first position.

2. The device according to claim 1, wherein:
- a relative position and a relative orientation between the first reference system and a reference system centered on the first inertial sensor is substantially constant, so that the first reference system is solidly connected to the reference system centered on the first inertial sensor;
- a relative position and a relative orientation between the second reference system and a reference system centered on the second inertial sensor is substantially constant so that the second reference system is solidly connected to the reference system centered on the second inertial sensor;
- the second calculating module is configured to calculate the relative orientation between the first reference system and the second reference system by analyzing directions of the vectors of the angular velocities acquired by the first and second inertial sensors, in a determined time interval.

3. The device according to claim 1, wherein the processing unit further comprises a compensating module configured to compensate a delay between flows of data detected by the first and second inertial sensors determining a synchronization, in input to the calculating module and the second calculating module, of the first and second data previously acquired by the acquiring module.

4. The device according to claim 1, wherein said processing unit further comprises a transforming module configured to:
receive in input data representing the first and second reference systems and one or more points in the corresponding reference systems, data representing the orientation calculated between the first and the second reference systems and the vector joining the origins of the first and second reference systems;
transform a point from a first of the reference systems towards a second of the reference systems.

5. The device according to claim 1, wherein the regulating device is structured to enable a regulation of the orientation in the space of the cutting guide with respect to the orthopaedic fixing system, to the second fixing component and as a function of the calculated vector.

6. The device according to claim 1, wherein the rigid body comprises a bone or an anatomical part of a limb.

7. The device according to claim 6, wherein:
the rigid body comprises a tibia;
the first fixing component is configured to be fixed to a proximal end of the tibia or to a tibial plateau;
the second fixing component is configured to be fixed to a distal end of the tibia or to a malleoli.

8. The device according to claim 1, wherein the second fixing component comprises a pliers structured for being fixed to the malleoli.

9. The device according to claim 8, wherein the pliers is structured for varying a distance between jaws thereof, with respect to the second reference system, or with respect to a position of a central point between the jaws.

10. A method for determining an axis joining origins of a first reference system and a second reference system of a rigid body, wherein relative positions and orientations of the first and second reference systems are not priorly known, the method comprising:
a) providing, on the rigid body, at least a first inertial sensor and a second inertial sensor, each provided with a triaxial accelerometer and a triaxial gyroscope;
b) constraining the first and second inertial sensors to the rigid body to respectively define the first and second reference system;
c) moving the rigid body so as to determine an angular displacement of the rigid body;
d) acquiring, by means of the first and second inertial sensors, first data representing angular velocities and second data representing linear accelerations of the rigid body during the movement of the rigid body;
e) calculating third data representing angular accelerations of the rigid body as a function of the acquired first data;
f) calculating a relative orientation between the first and the second reference systems as a function of the first data;
g) determining a primary vector which joins the origins of the first reference system and of the second reference system as a function of the first, second and third data and as a function of the relative orientation calculated between the first and second reference systems, wherein a primary direction of the primary vector is representative of the axis joining the origins of the first and second reference systems.

11. The method according to claim 10, further comprising:
receiving, in input, data representing said first and second reference systems;
receiving in input, one or more points in the corresponding first and second reference systems;
transforming a point from a first of the first and second reference systems towards a second of said first and second reference systems.

12. The method according to claim 10, further comprising:
fixing a first fixing component to a first end of the rigid body;
providing, on the first fixing component, an orthopaedic fixing system fixed to the first end of the rigid body with one or more pins;
providing, on the first fixing component, a cutting guide comprising a cutting tool and maintaining the cutting tool in a constant orientation;
providing, on the first fixing component, a regulating device structured to connect the cutting guide to the fixing system and to modify an orientation in a space of the cutting guide with respect to the fixing system;
mounting the first inertial sensor in a first position solidly constrained, in terms of orientation, to the cutting guide;
fixing a second fixing component to a second end of the rigid body at the second inertial sensor positioned in a second position different from the first position.

13. The method according to claim 12, further comprising regulating the orientation in the space of the cutting guide with respect to the orthopaedic fixing system, to the second fixing component and as a function of the calculated vector, by means of the regulating device.

* * * * *